(12) United States Patent
Wang et al.

(10) Patent No.: US 9,193,737 B2
(45) Date of Patent: Nov. 24, 2015

(54) PRODUCTION OF 6-HYDROXY MORPHINANS WITHOUT THE ISOLATION OF INTERMEDIATES

(71) Applicant: MALLINCKRODT LLC, Hazelwood, MO (US)

(72) Inventors: Peter X. Wang, Creve Coeur, MO (US); Tao Jiang, Chesterfield, MO (US)

(73) Assignee: Mallinckrodt LLC, Hazelwood, MO (US)

(*) Notice: Subject to any disclaimer, the term of this patent is extended or adjusted under 35 U.S.C. 154(b) by 0 days.

(21) Appl. No.: 14/533,522

(22) Filed: Nov. 5, 2014

(65) Prior Publication Data
US 2015/0126742 A1    May 7, 2015

Related U.S. Application Data

(60) Provisional application No. 61/901,032, filed on Nov. 7, 2013.

(51) Int. Cl.
 C07D 489/08    (2006.01)
 C07D 489/02    (2006.01)

(52) U.S. Cl.
 CPC .................... C07D 489/08 (2013.01)

(58) Field of Classification Search
 USPC ..................................... 546/44, 45
 See application file for complete search history.

(56) References Cited

U.S. PATENT DOCUMENTS

| | | | |
|---|---|---|---|
| 7,885,858 B2 | 2/2011 | Grote | |
| 7,985,858 B2 | 7/2011 | Grote | |
| 8,148,528 B2 | 4/2012 | Wang | |
| 8,168,790 B2 | 5/2012 | Bao | |
| 8,236,957 B2 | 8/2012 | Rezaie | |
| 8,261,719 B2 | 9/2012 | Grote | |
| 8,273,888 B2 | 9/2012 | Grote | |
| 8,309,727 B2 | 11/2012 | Wang | |
| 8,703,950 B2 * | 4/2014 | Keskeny et al. | 546/45 |
| 8,853,402 B2 | 10/2014 | Wilson | |
| 9,012,468 B2 | 4/2015 | Wang | |
| 9,073,933 B2 | 7/2015 | Chapman | |
| 2007/0172958 A1 | 7/2007 | Freiha | |
| 2009/0299069 A1 | 12/2009 | Wang | |
| 2010/0048905 A1 | 2/2010 | Wang | |
| 2010/0113788 A1 | 5/2010 | Grote | |
| 2010/0192921 A1 | 8/2010 | Grote | |
| 2012/0209002 A1 | 8/2012 | Wilson | |
| 2012/0259118 A1 | 10/2012 | Keskeny | |
| 2013/0005977 A1 | 1/2013 | Chapman | |
| 2013/0203999 A1 | 8/2013 | Wang | |

FOREIGN PATENT DOCUMENTS

| | | |
|---|---|---|
| EP | 0763038 B1 | 3/1999 |
| EP | 2426132 A1 | 7/2012 |
| WO | 2012003468 A1 | 1/2012 |
| WO | 2015069717 A1 | 5/2015 |

OTHER PUBLICATIONS

Hauser, 14-Hydroxycodeinone. An improved Synthesis. Journal of Medicinal Chemistry, 1974, p. 1117, vol. 17, No. 10.

* cited by examiner

*Primary Examiner* — Charanjit Aulakh

(57) ABSTRACT

The present invention provides a process for preparing a saturated 6,14-dihydroxy morphinan. The process comprises contacting an unsaturated 6-O-hydrocarbyl morphinan with hydrogen peroxide and an organic acid to form an unsaturated 6-keto-14-hydroxy morphinan. The unsaturated 6-keto-14-hydroxy morphinan is contacted with a first reducing agent to form an unsaturated 6,14-dihydroxy morphinan, and the unsaturated 6,14-dihydroxy morphinan is contacted with a second reducing agent to form the saturated 6,14-dihydroxy morphinan.

20 Claims, No Drawings

PRODUCTION OF 6-HYDROXY MORPHINANS WITHOUT THE ISOLATION OF INTERMEDIATES

CROSS-REFERENCE TO RELATED APPLICATIONS

This application claims the priority of U.S. Provisional Application Ser. No. 61/901,032, filed Nov. 7, 2013, which is hereby incorporated by reference in its entirety.

FIELD OF THE INVENTION

The present invention relates to processes for preparing alkaloids. The processes generally avoid the isolation of intermediate compounds produced in the multi-step synthesis of the alkaloid.

BACKGROUND OF THE INVENTION

Opioids, such as morphine, codeine, hydromorphone, hydrocodone, oxymorphone, and oxycodone, are important analgesics. Their dihydro-reduction products, the 6-hydroxy analogs such as 6α-hydromorphol, 6α-hydrocodol, 6α-oxymorphol, and 6α-oxycodol, also have analgesic effects along with other beneficial characteristics. Recently, polymer-functionalized 6-hydroxy opioid compounds have been reported to have sustained-release and abuse-resistant properties in addition to their common opioid analgesic effects. Patient enrollment for a Phase II clinical trial of PEGylated 6α-oxycodol is currently underway.

Producing hydroxy opioid compounds, however, generally proceeds through a number of steps, where each step requires isolation of the intermediate before the next synthetic step can be performed. For example, 6α-oxycodol can be prepared by reducing oxycodone, which itself was prepared from thebaine by oxidation followed by reduction, thus requiring three isolation steps. Isolation becomes necessary for a number of reasons, including the interference of reaction byproducts with later steps, which may lower the yield or halt the reaction altogether. But, isolation of intermediates itself is an extra step that can lower the yield and efficiency of the total synthesis. Thus, there is a need to develop a high yielding one-pot process for the multiple reaction steps in order to simplify operations so that production cost and cycle time may be reduced.

SUMMARY OF THE INVENTION

Briefly, therefore, one aspect of the present disclosure encompasses a process for preparing a saturated 6,14-dihydroxy morphinan. The process comprises contacting an unsaturated 6-O-hydrocarbyl morphinan with hydrogen peroxide and an organic acid to form an unsaturated 6-keto-14-hydroxy morphinan. The unsaturated 6-keto-14-hydroxy morphinan is contacted with a first reducing agent to form an unsaturated 6,14-dihydroxy morphinan; and the unsaturated 6,14-dihydroxy morphinan is contacted with a second reducing agent to form the saturated 6,14-dihydroxy morphinan.

A further aspect of the disclosure provides a process for preparing a compound comprising Formula (IV) from a compound comprising Formula (I). The process comprises contacting the compound comprising Formula (I) with hydrogen peroxide and a compound comprising formula $HOOCR^{18}$ to form a compound comprising Formula (II). The compound comprising Formula (II) is contacted with a first reducing agent to form a compound comprising Formula (III), and the compound comprising Formula (III) is contacted with a second reducing agent to form the compound comprising Formula (IV), according to the following reaction scheme:

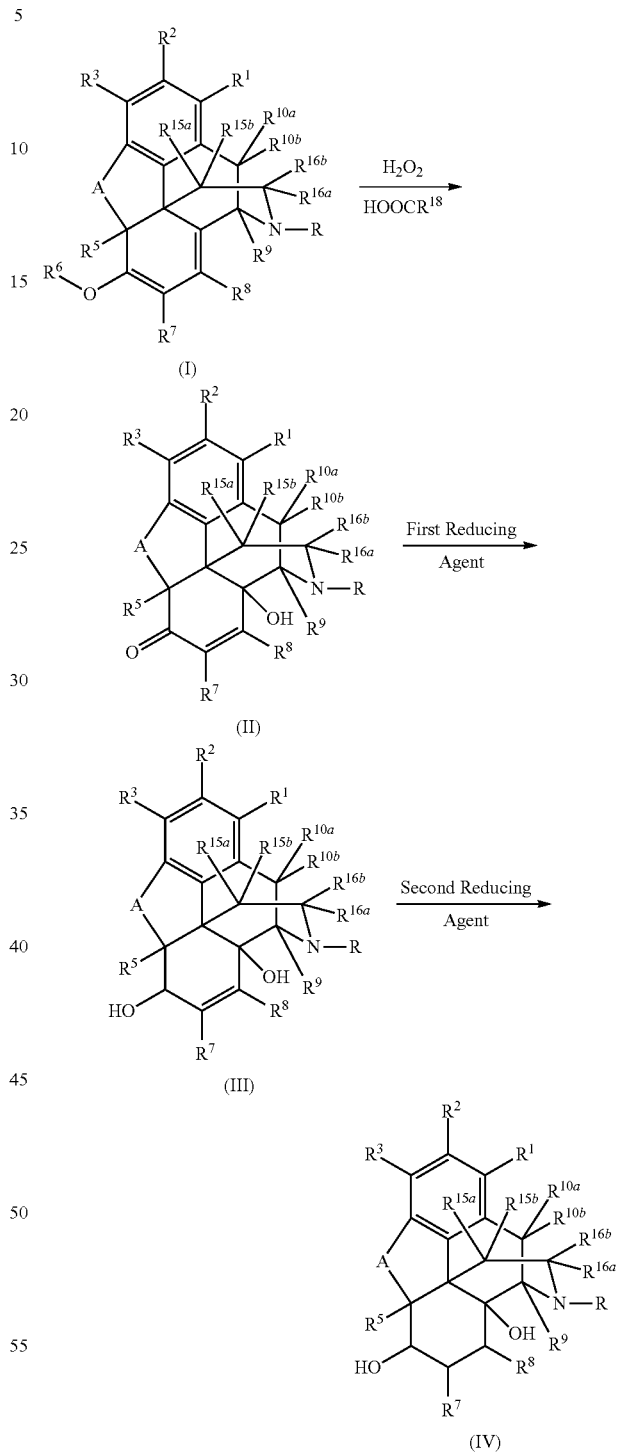

wherein:
A is selected from the group consisting of oxygen, sulfur, and nitrogen;
R is selected from the group consisting of hydrogen, hydrocarbyl, and substituted hydrocarbyl;
$R^1$, $R^2$, and $R^3$ are independently selected from the group consisting of hydrogen, amino, halogen, {—}OH, {—}OR$^{1611}$, {—}SH, {—}SR$^{1611}$, {—}NHR$^{1611}$, {—}NR$^{1611}$R$^{1612}$, hydrocarbyl, and substituted hydrocarbyl;

R$^5$, R$^7$, R$^8$, R$^9$, R$^{10a}$, R$^{10b}$, R$^{15a}$, R$^{15b}$, R$^{16a}$, and R$^{16b}$ are independently selected from the group consisting of hydrogen, amino, halogen, {—}OH, {—}OR$^{1611}$, {—}SH, {—}SR$^{1611}$, {—}NHR$^{1611}$, {—}NR$^{1611}$R$^{1612}$, hydrocarbyl, and substituted hydrocarbyl; wherein any pair of R$^{\#a}$ and R$^{\#b}$ wherein # is any one of 10, 15, and 16, optionally together form a moiety chosen from the group consisting of {=}O, {=}S, {=}CH$_2$, and {=}NR$^{1612}$;

R$^6$, R$^{1611}$, and R$^{1612}$ are independently selected from the group consisting of hydrocarbyl and substituted hydrocarbyl;

R$^{18}$ is selected from the group consisting of hydrogen, hydrocarbyl and substituted hydrocarbyl; and one or more of R$^1$, R$^2$, R$^3$, R$^5$, R$^6$, R$^7$, R$^8$, R$^9$, R$^{10a}$, R$^{10b}$, R$^{15a}$, R$^{15b}$, R$^{16a}$, and R$^{16b}$ may form part of a ring or ring system chosen from carbocyclic, substituted carbocyclic, heterocyclic, substituted heterocyclic, or combinations thereof.

Other features and iterations of the invention are described in more detail below.

DETAILED DESCRIPTION OF THE INVENTION

Disclosed herein are processes for preparing a saturated 6-hydroxy morphinan. The process comprises a one pot, multistep process in which no intermediate compounds are isolated. The first step of the process comprises contacting an unsaturated 6-O-hydrocarbyl morphinan comprising two carbon-carbon double bonds with hydrogen peroxide and an organic acid to form an unsaturated 6-keto-14-hydroxy morphinan containing one carbon-carbon double bond. During this step of the process, a peroxyacid, an effective oxidizing agent, is formed in situ by reaction of hydrogen peroxide with the organic acid. Forming peroxyacids in situ avoids problems associated with transporting, storing, and/or handling high concentrations of peroxyacids, such as peroxyacetic acid. Rather the peroxyacid is consumed during formation of the unsaturated 6-keto-14-hydroxy morphinan and never reaches dangerously high concentrations. Moreover, in embodiments in which the organic acid is formic acid, the formic acid not only functions as a catalyst without being consumed during the oxidation step, but it also serves as a hydrogen source later in the process during the final reduction step.

The next step of the process comprises contacting the unsaturated 6-keto-14-hydroxy morphinan with a first reducing agent to form an unsaturated 6,14-dihydroxy morphinan. For opioid compounds, reducing an α,β-unsaturated ketone typically is much more stereospecific for forming 6α-hydroxy compounds than reducing a saturated ketone. Thus, in the process disclosed herein, a 6α-hydroxy group is added by reducing the 6-keto-14-hydroxy morphinan, thereby forming the unsaturated 6,14-dihydroxy morphinan.

The last step of the process comprises contacting the unsaturated 6,14-dihydroxy morphinan with a second reducing agent to reduce the carbon-carbon double bond, thereby forming the saturated 6,14-dihydroxy morphinan. The second reducing agent may be a hydrogen transfer reagent, a combination of a hydrogen transfer reagent and a metal catalyst, or gaseous hydrogen and a metal catalyst. In embodiments, in which formic acid is used as the organic acid in the first step of the process, the formic acid may be used as a hydrogen donor in this step of the process. Typically, a transition metal catalyst (e.g., palladium on carbon) is added during this step of the one-pot process. Thus, the catalytic hydrogen transfer reaction not only reduces the carbon-carbon double bond, but also consumes excess formic acid in the reaction mixture such that less proton acceptor can be used to neutralize the reaction mixture and precipitate the final product. Moreover, the use of a hydrogen transfer reaction obviates the use of pressurized reactors and gaseous hydrogen.

(I) Process for Preparing Saturated 6,14-Dihydroxy Morphinans

One aspect of the disclosure encompasses a process for preparing a saturated 6,14-dihydroxy morphinan. The process comprises contacting an unsaturated 6-O-hydrocarbyl morphinan with hydrogen peroxide and an organic acid to form an unsaturated 6-keto-14-hydroxy morphinan. The unsaturated 6-keto-14-hydroxy morphinan is contacted with a first reducing agent to form an unsaturated 6,14-dihydroxy morphinan, and the unsaturated 6,14-dihydroxy morphinan is contacted with a second reducing agent to form the saturated 6,14-dihydroxy morphinan.

The unsaturated 6-O-hydrocarbyl morphinan may be thebaine or oripavine. The saturated 6,14-dihydroxy morphinan may be oxycodol or oxymorphol. The hydroxy group on C-14 of the saturated 6,14-dihydroxy morphinan may be removed, thereby forming hydromorphol or hydrocodol. The saturated 6-O-hydrocarbyl morphinan, the unsaturated 6-keto-14-hydroxy morphinan, the unsaturated 6,14-dihydroxy morphinan, and the saturated 6,14-dihydroxy morphinan may independently have an optical activity of (+) or (−). The 6-hydroxy group of the unsaturated or saturated 6,14-dihydroxy morphinan may have an alpha isomer to beta isomer ratio of at least 95:5. The reactant mixtures and reaction conditions for each step of the process are detailed below in section (II).

In general, the morphinans and normorphinans detailed herein include any compound comprising a morphinan structure as diagrammed below, wherein R is hydrocarbyl or substituted hydrocarbyl in morphinans, and R is hydrogen in normorphinans. For the purposes of illustration, the ring atoms of the core morphinan structure are numbered as shown below:

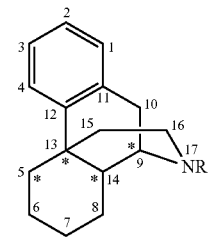

Morphinan compounds have asymmetric centers. In particular, the core morphinan compound may have at least four chiral carbons (designated by asterisks in the diagram above); namely, C-5, C-13, C-14, and C-9.

(II) Process for Preparing Compounds Comprising Formula (IV) from Compounds Comprising Formula (I)

This disclosure provides a process for preparing a compound comprising Formula (IV) from a compound comprising Formula (I). The process comprises contacting the compound comprising Formula (I) with hydrogen peroxide and a compound comprising formula HOOCR$^{18}$ to form a compound comprising Formula (II). The compound comprising Formula (II) is contacted with a first reducing agent to form a compound comprising Formula (III), and the compound comprising Formula (III) is contacted with a second reducing agent to form the compound comprising Formula (IV), according to the following reaction scheme:

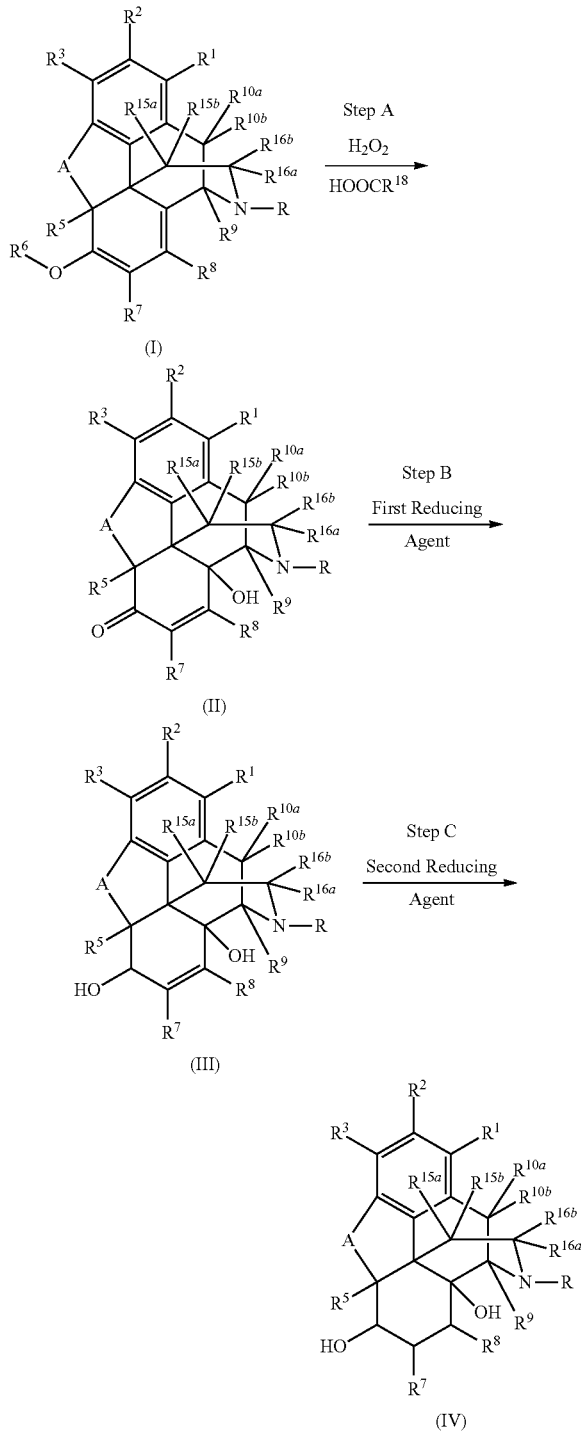

wherein:

A is selected from the group consisting of oxygen, sulfur, and nitrogen;

R is selected from the group consisting of hydrogen, hydrocarbyl and substituted hydrocarbyl;

$R^1$, $R^2$, and $R^3$ are independently selected from the group consisting of hydrogen, amino, halogen, {—}OH, {—}OR$^{1611}$, {—}SH, {—}SR$^{1611}$, {—}NHR$^{1611}$, {—}NR$^{1611}$R$^{1612}$, hydrocarbyl, and substituted hydrocarbyl;

$R^5$, $R^7$, $R^8$, $R^9$, $R^{10a}$, $R^{10b}$, $R^{15a}$, $R^{15b}$, $R^{16a}$, and $R^{16b}$ are independently selected from the group consisting of hydrogen, amino, halogen, {—}OH, {—}OR$^{1611}$, {—}SH, {—}SR$^{1611}$, {—}NHR$^{1611}$, {—}NR$^{1611}$R$^{1612}$, hydrocarbyl, and substituted hydrocarbyl; wherein any pair of R$^{\#a}$ and R$^{\#b}$ wherein # is any one of 10, 15, and 16, optionally together form a moiety chosen from the group consisting of {=}O, {=}S, {=}CH$_2$, and {=}NR$^{1612}$;

$R^6$, $R^{1611}$, and $R^{1612}$ are independently selected from the group consisting of hydrocarbyl and substituted hydrocarbyl;

$R^{18}$ is selected from the group consisting of hydrogen, hydrocarbyl and substituted hydrocarbyl; and one or more of $R^1$, $R^2$, $R^3$, $R^5$, $R^6$, $R^7$, $R^8$, $R^9$, $R^{10a}$, $R^{10b}$, $R^{15a}$, $R^{15b}$, $R^{16a}$, and $R^{16b}$ may form part of a ring or ring system chosen from carbocyclic, substituted carbocyclic, heterocyclic, substituted heterocyclic, or combinations thereof.

In one embodiment, R may be selected from the group consisting of hydrogen, alkyl, alkenyl, alkynyl, aryl, substituted alkyl, substituted alkenyl, substituted alkynyl, and substituted aryl. In another embodiment, $R^1$ and $R^2$ may be independently selected from the group consisting of hydrogen, amino, amine, halo, hydroxy, alkoxy, alkyl, alkenyl, alkynyl, aryl, substituted alkyl, substituted alkenyl, substituted alkynyl, and substituted aryl. In other embodiments, $R^3$ may be selected from the group consisting of hydroxy, alkoxy, hydrocarbyloxy, and substituted hydrocarbyloxy. In still other embodiments, $R^6$ may be selected from the group consisting of alkyl, alkenyl, alkynyl, aryl, substituted alkyl, substituted alkenyl, substituted alkynyl, and substituted aryl. In some embodiments, $R^5$, $R^7$, $R^8$, $R^9$, $R^{10a}$, $R^{10b}$, $R^{15a}$, $R^{15b}$, $R^{16a}$, $R^{16b}$ may be independently selected from the group consisting of hydrogen, amino, amine, halo, hydroxy, alkoxy, alkyl, alkenyl, alkynyl, aryl, substituted alkyl, substituted alkenyl, substituted alkynyl, and substituted aryl.

In an exemplary embodiment, A may be oxygen; $R^1$, $R^2$, $R^5$, $R^7$, $R^8$, $R^9$, $R^{10a}$, $R^{10b}$, $R^{15a}$, $R^{15b}$, $R^{16a}$, and $R^{16b}$, if present, may be hydrogen; R may be selected from the group consisting of hydrogen, methyl, cyclopropyl methyl, cyclobutyl methyl, and allyl; $R^3$ may be selected from the group consisting of hydroxy, alkoxy, aryloxy, substituted aryloxy, and protected hydroxy; and $R^6$ may be selected from the group consisting of alkyl, aryl, substituted alkyl, and substituted aryl.

In some embodiments, $R^{18}$ may be selected from the group consisting of hydrogen, alkyl, aryl, substituted alkyl, and substituted aryl. In an exemplary embodiment, $R^{18}$ may be selected from the group consisting of hydrogen, methyl, phenyl, and substituted phenyl. In a particular embodiment, $R^{18}$ may be hydrogen.

In some embodiments, the mole to mole ratio of the compound comprising Formula (I) to hydrogen peroxide to the compound comprising the formula HOOCR$^{18}$ may be from about 1:0.6:1 to about 1:2.2:8. In other embodiments, the process may be conducted in the presence of at least one polar protic solvent; and the volume to mass ratio of the solvent to the compound comprising Formula (I) may be from about 1:1 to about 4:1. In still other embodiments, the process may be conducted at a temperature from about 0° C. to about 70° C.

In other embodiments, the first reducing agent may comprise a borohydride. In exemplary embodiments, the first reducing agent may be selected from the group consisting of sodium borohydride and sodium triacetoxyborohydride. In some embodiments, the mole to mole ratio of the compound comprising Formula (II) to hydride from the first reducing agent may be from about 1:0.7 to about 1:5.

In some embodiments, the second reducing agent may be a hydrogen transfer reagent, a combination of a hydrogen transfer reagent and a metal catalyst, and hydrogen and a metal catalyst. In one embodiment, the second reducing agent may be a hydrogen transfer reagent, which is used in the presence of a transition metal catalyst. In an exemplary embodiment, the transition metal catalyst may be palladium supported on carbon. In some embodiments, the mole to mole ratio of the compound comprising Formula (III) to the hydrogen transfer reagent to the transition metal catalyst may be from about 1:0.1:0.002 to about 1:1:0.02.

In specific embodiments, steps (a), (b), and (c) may be conducted in a single reaction pot without isolation of the compounds comprising Formula (II) or Formula (III). In exemplary embodiments, the organic acid of the first step may be formic acid, the first reducing agent may be sodium borohydride or sodium triacetoxyborohydride, and the second reducing agent may be a hydrogen transfer reagent, such as, e.g., formic acid, which is used in the presence of a transition metal catalyst.

In other embodiments, the process may further comprise, after step (c), adjusting the pH to greater than about 8.7 to precipitate the compound comprising Formula (IV). In some other embodiments, the process may further comprise removing the hydroxyl group from C-14 of the compound comprising Formula (IV).

In still other embodiments, the compounds comprising Formulas (I), (II), (III), or (IV) may independently have an optical activity of (−) or (+); and the configuration of C-5, C-13, C-14, and C-9, respectively, is RRRR, RRSR, RRRS, RRSS, RSRR, RSSR, RSRS, RSSS, SRRR, SRSR, SRRS, SRSS, SSRR, SSSR, SSRS, or SSSS, provided that the C-15 and the C-16 carbons are both either on the alpha face of the molecule or the beta face of the molecule. In particular embodiments, the hydroxy group on C-6 of the compounds comprising Formulas (II) or (IV) may have an alpha isomer to beta isomer ratio of at least 95:5.

(a) Step A—Reaction Mixture

Step A of the process comprises contacting a compound comprising Formula (I) with hydrogen peroxide and a compound comprising formula $HOOCR^{18}$ to form a compound comprising Formula (II). The process commences with the formation of a reaction mixture comprising the compound comprising Formula (I), which is detailed above, hydrogen peroxide, a compound comprising formula $HOOCR^{18}$, and optionally a solvent system.

(i) Compound Comprising the Formula $HOOCR^{18}$ and Hydrogen Peroxide

A variety of organic acids are suitable for use in this process. In general, the organic acid is represented by the formula $HOOCR^{18}$, wherein $R^{18}$ may be selected from the group consisting of hydrogen, hydrocarbyl, and substituted hydrocarbyl. In some embodiments, $R^{18}$ is selected from the group consisting of hydrogen, alkyl, aryl, substituted alkyl, and substituted aryl. In other embodiments, $R^{18}$ is selected from the group consisting of hydrogen, methyl, phenyl, and substituted phenyl. In a particular embodiment, $R^{18}$ is hydrogen. Non-limiting example of suitable organic acids include formic acid, acetic acid, benzoic acid, and chlorobenzoic acid. In exemplary embodiments, the organic acid is formic acid.

The amounts of the organic acid (i.e., the compound comprising formula $HOOCR^{18}$) and hydrogen peroxide that are contacted with the compound comprising Formula (I) may vary. In general, the mole to mole ratio of the compound comprising Formula (I) to hydrogen peroxide to the organic acid may range from about 1:0.1:0.2 to about 1:11:40. In various embodiments, the mole to mole ratio of the compound comprising Formula (I) to hydrogen peroxide to organic acid may range from about 1:0.1:0.2 to about 1:0.5:1, about 1:0.5:1 to about 1:0.8:1.5, about 1:0.8:1.5 to about 1:1:2, about 1:1:2 to about 1:2:4, about 1:2:4 to about 1:4:8, from about 1:4:8 to about 1:8:16, or from about 1:8:16 to about 1:11:40. In exemplary embodiments, the mole to mole ratio of the compound comprising Formula (I) to hydrogen peroxide to the compound comprising the formula $HOOCR^{18}$ may be from about 1:0.6:1 to about 1:2.2:8.

(ii) Solvent

The reaction is generally conducted in the presence of a solvent or solvent system. The solvent may be a polar protic solvent, a polar aprotic solvent, or a nonpolar organic solvent. Non-limiting examples of suitable protic polar solvents include water; alcohols such as methanol, ethanol, isopropanol, n-propanol, isobutanol, n-butanol, s-butanol, t-butanol, and the like; diols such as propylene glycol; organic acids such as formic acid, acetic acid, and so forth; amides such as formamide, acetamide, and the like; and combinations of any of the above. Non-limiting examples of suitable aprotic solvents include acetone, acetonitrile, diethoxymethane, N,N-dimethylformamide (DMF), dimethyl sulfoxide (DMSO), N,N-dimethylpropanamide (or dimethylpropionamide; DMP), 1,3-dimethyl-3,4,5,6-tetrahydro-2(1H)-pyrimidinone (DMPU), 1,3-dimethyl-2-imidazolidinone (DMI), 1,2-dimethoxyethane (DME), dimethoxymethane, bis(2-methoxyethyl)ether, N,N-dimethylacetamide (DMA), N-methyl-2-pyrrolidinone (NMP), 1,4-dioxane, ethyl formate, formamide, hexachloroacetone, hexamethylphosphoramide, methyl acetate, N-methylacetamide, N-methylformamide, methylene chloride, methoxyethane, morpholine, nitrobenzene, nitromethane, propionitrile, pyridine, sulfolane, tetramethylurea, tetrahydrofuran (THF), 2-methyl tetrahydrofuran, tetrahydropyran, trichloromethane, and combinations thereof. Representative nonpolar solvents include, but are not limited to, alkane and substituted alkane solvents (including cycloalkanes), aromatic hydrocarbons, esters, ethers, ketones, and combinations thereof. Specific polar protic solvents that may be employed include, for example, water, formic acid, acetic acid, methanol, ethanol, propanol, isopropanol, and combinations thereof.

In general, the volume to mass ratio of the solvent to the compound comprising Formula (I) ranges from about 0.5:1 to about 100:1. In various embodiments, the volume to mass ratio of the solvent to the compound comprising Formula (I) may range from about 0.5:1 to about 5:1, from about 5:1 to about 25:1, or from about 25:1 to about 100:1. In certain embodiments, the volume to mass ratio of the solvent to the compound comprising Formula (I) may range from about 1:1 to about 20:1.

(b) Step A—Reaction Conditions

In general, the reaction is conducted at a temperature that ranges from about 0° C. to about 100° C. In various embodiments, the reaction may be conducted at a temperature from about 0° C. to about 20° C., from about 20° C. to about 40° C., from about 40° C. to about 60° C., from about 60° C. to about 80° C., or from about 80° C. to about 100° C. In some embodiments, the temperature of the reaction may range from 0° C. to about 70° C. In certain embodiments, the temperature of the reaction may range from about 20° C. to about 35° C. In other embodiments, the reaction may be conducted at a first temperature of about 20° C. to about 35° C. and then a second temperature of about 45° C. to about 55° C. The reaction may be conducted in the presence of air, or the reaction may be conducted under an inert atmosphere (e.g., under nitrogen or argon). Typically, the reaction is conducted under ambient pressure.

Typically, the reaction is allowed to proceed for a sufficient period of time until the reaction is complete, as determined by chromatography (e.g., HPLC) or another suitable method. In this context, a "completed reaction" generally means that the reaction mixture contains a significantly diminished amount of the compound comprising Formula (I), and a significantly increased amount of the compound comprising Formula (II) compared to the amounts of each present at the beginning of the reaction. Typically, the amount of the compound comprising Formula (I) remaining in the reaction mixture after the reaction is complete may be less than about 3%, or less than about 1%. In general, the reaction may proceed for about 1 hour to about 48 hours. Typically, the duration of the reaction is longer at lower reaction temperatures. In certain embodiments, the reaction may be allowed to proceed for about a period of time ranging from about 1 hour to about 3 hours, from about 3 hours to about 6 hours, from about 6 hours to about 12 hours, from about 12 hours to about 18 hours, from about 18 hours to about 24 hours, from about 24 hours to about 36 hours, or from about 36 hours to about 48 hours. In exemplary embodiments, the reaction may be allowed to proceed for about 12 hours to about 18 hours.

Generally, the compound comprising Formula (II) is not isolated and step (b) of the process proceeds in the same reaction pot or reactor. In some embodiments, the compound comprising Formula (II) may be isolated from the reaction mixture using techniques known to those of skill in the art. Non-limiting examples of suitable techniques include precipitation, extraction, evaporation, distillation, chromatography, and crystallization.

The yield of the compound comprising Formula (II) can and will vary. Typically, the yield of the compound comprising Formula (II) may be at least about 40%. In one embodiment, the yield of the compound comprising Formula (II) may range from about 40% to about 60%. In another embodiment, the yield of the compound comprising Formula (II) may range from about 60% to about 80%. In a further embodiment, the yield of the compound comprising Formula (II) may range from about 80% to about 90%. In still another embodiment, the yield of the compound comprising Formula (II) may be greater than about 90%, or greater than about 95%.

(c) Step B—Reaction Mixture

The process further comprises contacting the compound comprising Formula (II) with a first reducing agent to form a compound comprising Formula (III). The process commences with the formation of a reaction mixture comprising the compound comprising Formula (II), which is detailed above, a first reducing agent, and optionally a solvent system.

(i) First Reducing Agent

In some embodiments, the first reducing agent may comprise a borohydride, for example selected from the group consisting of borane/tetrahydrofuran, borane/dimethyl sulfide, sodium borohydride, lithium borohydride, potassium borohydride, sodium cyanoborohydride, sodium triacetoxyborohydride, tetra(n-butyl)-ammonium borohydride, lithium triethylborohydride, potassium tri(sec-butyl)borohydride, potassium tri(siamyl)borohydride, lithium (sec-butyl)borohydride, lithium tri(siamyl)borohydride, sodium tri(sec-butyl)borohydride, lithium aminoborohydride, sodium dimethylaminoborohydride, lithium diethylaminoborohydride, lithium di-n-propylaminoborohydride, lithium diisopropylaminoborohydride, lithium-1-azaheptanoborohydride, lithium pyrrolidinoborohydride, lithium morpholinoborohydride, lithium piperidinoborohydride, and lithium (N-ethyl-N-phenyl-amino) borohydride. In exemplary embodiments, the first reducing agent may be sodium borohydride or sodium triacetoxyborohydride.

The amount of first reducing agent added to the reaction mixture can and will vary. In general, the mole to mole ratio of the compound comprising Formula (II) to the first reducing agent may range from about 1:0.15 to about 1:25. In certain embodiments, the mole to mole ratio of the compound comprising Formula (II) to the first reducing agent may range from about 1:0.15 to about 1:0.7, from about 1:0.7 to about 1:1.5, from about 1:1.5 to about 1:2.5, from about 1:2.5 to about 1:5, from about 1:5 to about 1:10, from about 1:10 to about 1:15, from about 1:15 to about 1:20, or from about 1:20 to about 1:25. In certain embodiments, the mole to mole ratio of the compound comprising Formula (II) to first reducing agent may range from about 1:0.7 to about 1:5.

When the first reducing agent is a hydride source, such as a borohydride, the mole to mole ratio may be calculated as based on the molar equivalents of hydride provided by the hydride source. For example, one mole of sodium borohydride provides four moles of hydride, whereas one mole of sodium triacetoxyborohydride provide one mole of hydride. One of ordinary skill in the art would be able to calculate the molar equivalents of hydride based, for example, on the chemical formula of the first reducing agent. As such, in certain embodiments, the mole to mole ratio of the compound comprising Formula (II) to hydride from the first reducing agent may range from about 1:0.15 to about 1:0.7, from about 1:0.7 to about 1:1.5, from about 1:1.5 to about 1:2.5, from about 1:2.5 to about 1:5, from about 1:5 to about 1:10, from about 1:10 to about 1:15, from about 1:15 to about 1:20, or from about 1:20 to about 1:25. In certain embodiments, the mole to mole ratio of the compound comprising Formula (II) to hydride from the first reducing agent may range from about 1:0.7 to about 1:5.

Contact with the first reducing agent generally is conducted in the presence of a solvent or solvent system. Suitable solvents and solvent systems are detailed above in section (II)(a)(ii). In exemplary embodiments, the solvent system may comprise water, formic acid, acetic acid, methanol, ethanol, propanol, isopropanol, or combinations thereof.

In general, the volume to mass ratio of the solvent to the compound comprising Formula (II) ranges from about 0.5:1 to about 100:1. In various embodiments, the volume to mass ratio of the solvent to the compound comprising Formula (II) may range from 0.5:1 to about 5:1, from about 5:1 to about 25:1, or from about 25:1 to about 100:1. In exemplary embodiments, the volume to mass ratio of the solvent to the compound comprising Formula (II) may range from about 1:1 to about 20:1.

(d) Step B—Reaction Conditions

The temperature at which the reaction is conducted can and will vary. In general, the temperature of the reaction will range from about 0° C. to about 100° C. In various embodiments, the temperature of the reaction may range from about from about 0° C. to about 20° C., from about 20° C. to about 40° C., from about 40° C. to about 60° C., from about 60° C. to about 80° C., or from about 80° C. to about 100° C. In some reactions, the temperature of the reaction may range from about 0° C. to about 70° C. In specific embodiments, the temperature of the reaction may be less than about 30° C. In general, the reaction is conducted under an inert atmosphere (e.g., under nitrogen or argon) and ambient pressure.

Typically, the reaction is allowed to proceed for a sufficient period of time until the reaction is complete, as detailed above. In a completed reaction, the amount of the compound comprising Formula (II) remaining in the reaction mixture may be less than about 3%, or less than about 1%. In general, the reaction may proceed for about 1 hour to about 24 hours. In some embodiments, the reaction may proceed for about 1 hour to about 3 hours, from about 3 hours to about 4 hours, from about 4 hours to about 6 hours, from about 6 hours to about 8 hours, from about 8 hours to about 12 hours, from about 12 hours to about 18 hours, or from about 18 hours to about 24 hours. In exemplary embodiments, the reaction may be allowed to proceed about 4 hours to about 6 hours.

Generally, the compound comprising Formula (III) is not isolated and step (c) of the process proceeds in the same reaction pot or reactor. In some embodiments, the compound comprising Formula (III) may be isolated from the reaction mixture using techniques known to those of skill in the art. Non-limiting examples of suitable techniques include precipitation, extraction, evaporation, distillation, chromatography, and crystallization.

The yield of the compound comprising Formula (III) can and will vary. Typically, the yield of the compound comprising Formula (III) may be at least about 35%. In one embodiment, the yield of the compound comprising Formula (III) may range from about 35% to about 65%. In another embodiment, the yield of the compound comprising Formula (III) may range from about 65% to about 75%. In yet another embodiment, the yield of the compound comprising Formula (III) may range from about 75% to about 85%. In a further embodiment, the yield of the compound comprising Formula (III) may range from about 85% to about 95%. In still another embodiment, the yield of the compound comprising Formula (III) may be greater than about 95%.

(e) Step C—Reaction Mixture

The process further comprises contacting the compound comprising Formula (III) with a second reducing agent to form a compound comprising Formula (IV). The process commences with the formation of a reaction mixture comprising the compound comprising Formula (III), which is detailed above, a second reducing agent, and optionally a solvent system.

(i) Second Reducing Agent

A variety of reducing agents may be used in the step of the process. For example, the second reducing agent may be a hydrogen transfer reagent, a combination of a hydrogen transfer reagent and a metal catalyst, or gaseous hydrogen and a metal catalyst (under pressure, e.g., 60 psi).

In some embodiments, the second reducing agent may be a hydrogen transfer reagent such that the double bond is reduced by a hydrogen transfer reaction. In general, a hydrogen transfer reagent comprises an oxygen or nitrogen atom linked to one or more hydrogen atoms. Non-limiting examples of suitable hydrogen transfer reagents include formic acid, formate salts (e.g., ammonium formate), alcohols (e.g., methanol, ethanol, isopropanol, etc.), diols (e.g., glycerol), and amines (e.g., trithethylamine, ethanolamine, and the like). In exemplary embodiments, the hydrogen transfer reagent is formic acid.

The amount of hydrogen transfer reagent contacted with the compound comprising Formula (III) can and will vary. In general, the mole to mole ratio of the compound comprising Formula (III) to the hydrogen transfer reagent may range from about 1:0.05 to about 1:10. In various embodiments, the mole to mole ratio of the compound comprising Formula (III) to the hydrogen transfer reagent range from about 1:0.05 to about 1:0.2, from about 1:0.2 to about 1:1, from about 1:1 to about 1:4, or from about 1:4 to about 1:10. In exemplary embodiments, the mole to mole ratio of the compound comprising Formula (III) to the hydrogen transfer reagent may range from about 1:0.1 to about 1:1.

A variety of metal catalysts are suitable for use with the hydrogen transfer reagent (or with gaseous hydrogen). In some embodiments, the metal catalyst may be a transition metal catalyst. As used herein, the term "transition metal catalyst" refers to a transition metal element, transition metal salt, or a transition metal complex. In general, the transition metal may be any transition metal. In some embodiments, the transition metal may be iridium, iron, nickel, osmium, palladium, platinum, ruthenium and rhodium. In one exemplary embodiment, the transition metal may be ruthenium, iridium, or rhodium. A skilled artisan appreciates that the oxidation state of transition metal may vary, and may be, for example, (0), (I), (II), (III), (IV), (V), (VI) or (VII). For example, non-limiting examples of suitable transition metals include ruthenium(0), ruthenium(II), ruthenium(III), ruthenium(IV), rhodium(0), rhodium(I), rhodium(III), iridium(0), iridium (III), iridium(IV), palladium(0), palladium(II), palladium (IV), platinum(0), platinum(II), platinum(IV), and nickel(0).

In some embodiments, the transition metal catalyst may be the transition metal element itself. For example, the transition metal element may be a powder or a sponge, such as, e.g., ruthenium powder, rhodium powder, ruthenium sponge, rhodium sponge, palladium sponge, and so forth. Alternatively, the transition metal element may be rhodium black, ruthenium black, palladium black, etc. In still other embodiments, the transition metal element may be immobilized on a solid surface or support. Suitable examples include, but are not limited to, ruthenium on carbon, rhodium on carbon, palladium on carbon, ruthenium on alumina, rhodium on alumina, platinum on alumina, palladium on alumina, rhodium on silica, palladium on silica, palladium on charcoal, palladium on pumice, and so forth. In exemplary embodiments, the transition metal catalyst may be palladium supported on carbon.

In other embodiments, the transition metal catalyst may be a transition metal salt. Non-limiting examples of suitable salts include acetates, acetyacetonates, alkoxides, butyrates, carbonyls, dioxides, halides, hexonates, hydrides, mesylates, octanates, nitrates, nitrosyl halides, nitrosyl nitrates, sulfates, sulfides, sulfonates, phosphates, trifluoromethanesulfonates, trimethylacetates, tosylates, and combinations thereof. Non-limiting examples of suitable transition metal salts include $RuCl_3$, $RuBr_3$, $Ru(CF_3SO_3)_2$, $Ru_2(SO_4)_3$, $Ru(NO_3)_3$, $Ru(OAc)_3$, $PdCl_2$, $Pd(OAc)_2$, $RhCl_3$, $RhBr_3$, $Rh_2(SO_4)_3$, $(Rh(CO_2)Cl)_2$, $Rh_2(SO_4)_3$, $Rh_2(OAC)_4$, $IrCl_3$, and $OsCl_3$. The transition metal salt may be soluble (i.e., homogeneous). Alternatively, the transition metal salt may be immobilized on a solid support (i.e., heterogeneous). The transition metal salt may be immobilized on the solid support via noncovalent or covalent bonds. In some embodiments, the solid support may be an inorganic material. Suitable inorganic materials include silicas, alumina, titania, carbondium, zirconia, activated charcoal, zeolites, clays, polymers, ceramics, and activated carbon. Suitable silicas include silicon dioxide, amorphous silica, and microporous or mesoporous silicas. In other embodiments, the solid support may be a polymer. The polymer may be a natural polymer, a synthetic polymer, a semi-synthetic polymer, or a copolymer. Non-limiting examples of polymers include agarose, cellulose, nitrocellulose, methyl cellulose, polyacrylic, polyacrylamide, polyacrylonitrile, polyamide, polyether, polyester, polyethylene, polystyrene, polysulfone, polyvinyl chloride, polyvinylidene, methacrylate copolymer, and polystyrene-vinyl chloride copolymer.

In further embodiments, the transition metal catalyst may be a transition metal complex. In general, a transition metal complex comprises the transition metal and 4, 5, or 6 coordinate species with oxidation states ranging from 0 to 8. The complexes may be ionic, or the complexes may comprise covalently bound ligands and counter ions. Alternatively, the complexes may comprise a mixture of ionic and covalent bonds between the metal, ligand(s), and/or counter ion(s). The ligand may be monodentate or polydentate. Non-limiting examples of suitable ligands include arene ligands, olefin ligands, alkyne ligands, heterocycloalkyl ligands, heteroaryl ligands, alkyl ligands, cyclopentadienyl ligands, hydride ligands, amine ligands, carbonyl ligands, nitrogen donor ligands, phosphorous donor ligands, oxygen donor ligands, and so forth. The ligand may also be a solvent such as, e.g., DMSO, methanol, methylene chloride, tetrahydrofuran, acetone, ethanol, pyridine, or a tetraalkylammonia compound. Suitable counter ions include, but are not limited to, halides, $BF_4$, $PF_6$, $ClO_4$, $CHO_2$, $CF_3SO_3$, $CH_3CO_2$, $ArCO_2$, $CH_3SO_3$, p-tolyl$SO_3$, $HSO_4$, $H_2PO_4$, and hydrocarbyl anions. Numerous transition metal complexes are detailed in "Transposition of Allylic Alcohols into Carbonyl Compounds Mediated by Transition Metal Complexes" by Uma et al., Chem. Rev. 103: 27-51 (2003).

The transition metal complex may be soluble (i.e., homogeneous). Alternatively, the transition metal complex may be immobilized on a solid support (i.e., heterogeneous). The transition metal complex may be immobilized on the solid support via noncovalent or covalent bonds. Examples of suitable solid supports are presented above.

The amount of transition metal catalyst used in a hydrogen transfer reaction can and will vary. In general, the mole to mole ratio of the compound comprising Formula (III) to the transition metal catalyst may range from about 1:0.0004 to about 1:0.08 In certain embodiments, the mole to mole ratio of the compound comprising Formula (III) to the transition metal catalyst may range from about 1:0.0004 to about 1:0.001, from about 1:0.001 to about 1:0.003, from about 1:0.003 to about 1:0.01, from about 1:0.01 to about 1:0.03, or from about 1:0.03 to about 1:0.08. In certain embodiments, the mole to mole ratio of the compound comprising Formula (III) to the transition metal catalyst may range from about 1:0.002 to about 1:0.02. When the transition metal catalyst is immobilized on an inert support, such as carbon, the mole to mole ratio of the transition metal catalyst may be based on the percentage of transition metal present in the catalyst rather than the total weight of the catalyst including the weight of the support. One of ordinary skill would be able to calculate the mole to mole ratio using techniques common in the art.

Contact with the second reducing agent generally is conducted in the presence of a solvent or solvent system. Suitable solvents and solvent systems are detailed above in section (II)(a)(ii). In exemplary embodiments, the solvent system may comprise water, formic acid, acetic acid, methanol, ethanol, propanol, isopropanol, or combinations thereof.

In general, the volume to mass ratio of the solvent to the compound comprising Formula (III) ranges from about 0.5:1 to about 100:1. In various embodiments, the volume to mass ratio of the solvent to the compound comprising Formula (III) may range from 0.5:1 to about 5:1, from about 5:1 to about 25:1, or from about 25:1 to about 100:1. In exemplary embodiments, the volume to mass ratio of the solvent to the compound comprising Formula (III) may range from about 1:1 to about 20:1.

(f) Step C—Reaction Conditions

The temperature at which the reaction is conducted can and will vary. In general, the temperature of the reaction will range from about 0° C. to about 100° C. In various embodiments, the temperature of the reaction may range from about 0° C. to about 25° C., from about 25° C. to about 50° C., from about 50° C. to about 75° C., or from about 75° C. to about 100° C. In some embodiments, the temperature of the reaction may range from about 0° C. to about 70° C. In specific embodiments, the temperature of the reaction may range from about 40° C. to about 70° C., or from about 50° C. to about 60° C. In general, the reaction is conducted under an inert atmosphere (e.g., under nitrogen or argon). In embodiments, in which the second reducing agent comprises a hydrogen transfer reagent, the reaction is conducted under ambient pressure.

Typically, the reaction is allowed to proceed for a sufficient period of time until the reaction is complete, as detailed above. In a completed reaction, the amount of the compound comprising Formula (III) remaining in the reaction mixture may be less than about 3%, or less than about 1%. In general, the reaction may proceed for about 1 hour to about 24 hours. In some embodiments, the reaction may proceed for about 1 hour to about 3 hours, from about 3 hours to about 4 hours, from about 4 hours to about 6 hours, from about 6 hours to about 8 hours, from about 8 hours to about 12 hours, from about 12 hours to about 18 hours, or from about 18 hours to about 24 hours. In exemplary embodiments, the reaction may be allowed to proceed for about 4 hours to about 8 hours.

The compound comprising Formula (IV) may be isolated from the reaction mixture using techniques known to those of skill in the art. Non-limiting examples of suitable techniques include precipitation, extraction, evaporation, distillation, chromatography, and crystallization. The compound comprising Formula (IV) may be used as is, or may be converted to another compound using techniques familiar to those of skill in the art.

The yield of the compound comprising Formula (IV) can and will vary. Typically, the yield of the compound comprising Formula (IV) may be at least about 35%. In one embodiment, the yield of the compound comprising Formula (IV) may range from about 35% to about 65%. In another embodiment, the yield of the compound comprising Formula (IV) may range from about 65% to about 75%. In yet another embodiment, the yield of the compound comprising Formula (IV) may range from about 75% to about 85%. In a further embodiment, the yield of the compound comprising Formula (IV) may range from about 85% to about 95%. In still another embodiment, the yield of the compound comprising Formula (IV) may be greater than about 95%.

(g) Further Optional Steps

The process may further comprise additional steps after forming a compound of Formula (IV). For example, in some embodiments, the pH may be adjusted to greater than 10 to precipitate the compound comprising Formula (IV). In other embodiments, the process may further comprise removing the hydroxyl group from C-14 of the compound comprising Formula (IV).

(i) Precipitation

In some embodiments, the process may further comprise adjusting the pH to greater than about 8.7 to precipitate the compound comprising Formula (IV). The pH may be adjusted, for example, by adding the appropriate amount of a suitable proton acceptor to the reaction mixture containing the compound comprising Formula (IV). The proton acceptor typically has a pKa between about 7 and about 13. Suitable proton acceptors having this characteristic include hydroxide salts (such as, for example, NaOH, KOH, or $Mg(OH)_2$); hydrides (such as, for example, ammonium hydride, sodium hydride, sodium amide, and the like), borate salts (such as, for example, $NaBO_3$), di- and tri-basic phosphate salts (such as, for example, $Na_2HPO_4$ and $Na_3PO_4$, and the like), bicarbonate salts (such as, for example, $NaHCO_3$, $KHCO_3$, $LiCO_3$, and the like), carbonate salts (such as, for example, $Na_2CO_3$, $K_2CO_3$, $Li_2CO_3$, and the like), organic bases (such as, for example, pyridine, triethylamine, diisopropylethylamine, N-methylmorpholine, N,N-dimethylaminopyridine), and mixtures of any of the above. In exemplary embodiments the proton acceptor may comprise a hydroxide, such as sodium hydroxide or ammonium hydride.

The amount of proton acceptor added to the reaction mixture comprising may vary. In general, the amount of proton acceptor is added to achieve a pH greater than about 8.7, for example, a pH of about 9.0, about 9.5, about 10., about 10.5, about 11, about 12, or about 13. In some embodiments, the target pH is achieve by selecting the mole to mole ratio of the compound comprising Formula (IV) to the proton acceptor, which may range from about 1:0.5 to about 1:10. In various embodiments, mole to mole ratio of the compound comprising Formula (IV) to the proton acceptor may range from about 1:0.5 to about 1:2, from about 1:2 to about 1:5, or from about 1:5 to about 1:10. In exemplary embodiments, the mole to mole ratio of the compound comprising Formula (IV) to the proton acceptor may range from about 1:1 to about 1:4.

In some embodiments, the reaction mixture may further comprise a solvent. Suitable solvents and ratios of solvent to the starting substrate are listed above in section (II)(a)(ii). In exemplary embodiments, the solvent may be a polar protic solvent, and the volume to mass ratio of the solvent to the compound comprising Formula (IV) may range from about 2:1 to about 20:1.

In general, the reaction is conducted at a temperature that ranges from about 0° C. to about 100° C. In various embodiments, the reaction may be conducted at a temperature from about 0° C. to about 20° C., from about 20° C. to about 40° C., from about 40° C. to about 60° C., from about 60° C. to about 80° C., from about 80° C. to about 100° C. The reaction generally is performed under ambient pressure. In general, the reaction may proceed for about 2 hours to about 24 hours. In some embodiments, the reaction may proceed for about 2 hours to about 6 hours, from about 6 hours to about 12 hours, or from about 12 hours to about 24 hours.

In general, the yield of the precipitated compound comprising the Formula (IV) will be at least about 40% by weight. In certain embodiments, the yield of the precipitated compound comprising Formula (IV) may be at least about 60%, at least about 70%, at least about 80%, at least about 90%, or at least about 95%.

(ii) Dehydration

In other embodiments, the process may further comprise removing the hydroxyl group from C-14 of the compound comprising Formula (IV). In some embodiments, the hydroxyl group is removed from C-14 by contacting the compound comprising Formula (IV) with an appropriate amount of a suitable proton donor. One of ordinary skill in the art would recognize other suitable reagents and methods for dehydrating a compound comprising Formula (IV).

In general, the proton donor has a pKa of less than about 9, for example a pKa of less than about 6. Suitable proton donors having a pKa less than about 6 include, but are not limited to, HOAc, HCO$_2$H, H$_2$CO$_3$, MeSO$_3$H, poly H$_3$PO$_4$, H$_3$PO$_4$, H$_2$SO$_4$, HCl, HBr, HI, CF$_3$SO$_3$H, and p-methyltoluenesulfonic acid. Suitable proton donors having a pKa less than about 0 include, but are not limited to, MeSO$_3$H, poly H$_3$PO$_4$, H$_3$PO$_4$, H$_2$SO$_4$, HCl, HBr, HClO$_4$, HI, HNO$_3$, CF$_3$SO$_3$H, p-methyltoluenesulfonic acid, HClO$_3$, HBrO$_4$, HIO$_3$, and HIO$_4$.

The amount of proton donor added to the reaction may vary. In general, the mole to mole ratio of the of the compound comprising Formula (IV) to the proton donor ranges from about 1:0.05 to about 1:10. In various embodiments, mole to mole ratio of the compound comprising Formula (IV) to the proton donor may range from about 1:0.05 to about 1:1, from about 1:1 to about 1:5, or from about 1:5 to about 1:10. In exemplary embodiments, the mole to mole ratio of the compound comprising Formula (IV) to the proton donor may range from about 1:0.1 to about 1:5.

In some embodiments, the reaction mixture may further comprise a solvent. Suitable solvents and ratios of solvent to the starting substrate are listed above in section (II)(a)(ii). In exemplary embodiments, the solvent may be a polar protic solvent, and the volume to mass ratio of the solvent to the compound comprising Formula (IV) may range from about 2:1 to about 20:1.

Typically, the reaction is allowed to proceed for a sufficient period of time until the reaction is complete, as detailed above. In a completed reaction, the amount of the compound comprising Formula (IV) remaining in the reaction mixture may be less than about 3%, or less than about 1%. In general, the reaction is conducted at a temperature that ranges from about 0° C. to about 100° C. In various embodiments, the reaction may be conducted at a temperature from about 0° C. to about 20° C., from about 20° C. to about 40° C., from about 40° C. to about 60° C., from about 60° C. to about 80° C., from about 80° C. to about 100° C. The reaction generally is performed under ambient pressure. In general, the reaction may proceed for about 2 hours to about 24 hours. In some embodiments, the reaction may proceed for about 2 hours to about 6 hours, from about 6 hours to about 12 hours, or from about 12 hours to about 24 hours.

The dehydration product may be isolated from the reaction mixture using techniques known to those of skill in the art. Non-limiting examples of suitable techniques include precipitation, extraction, evaporation, distillation, chromatography, and crystallization. The dehydration product may be used as is, or may be converted to another compound using techniques familiar to those of skill in the art.

The yield of the dehydration product can and will vary. Typically, the yield of the dehydration product may be at least about 35%. In one embodiment, the yield of the dehydration product may range from about 35% to about 65%. In another embodiment, the yield of the dehydration product may range from about 65% to about 75%. In yet another embodiment, the yield of the dehydration product may range from about 75% to about 85%. In a further embodiment, the yield of the dehydration product may range from about 85% to about 95%. In still another embodiment, the yield of the dehydration product may be greater than about 95%.

(h) Exemplary Embodiments

In certain embodiments, the process consists of preparing a compound comprising Formula (IVa) from a compound comprising Formula (Ia). The process comprises contacting the compound comprising Formula (Ia) with hydrogen peroxide and a compound comprising formula HOOCR$^{18}$ to form a compound comprising Formula (IIa). The compound comprising Formula (IIa) is contacted with a first reducing agent to form a compound comprising Formula (IIIa), and the compound comprising Formula (IIIa) is contacted with a second reducing agent to form the compound comprising Formula (IVa), according to the following reaction scheme:

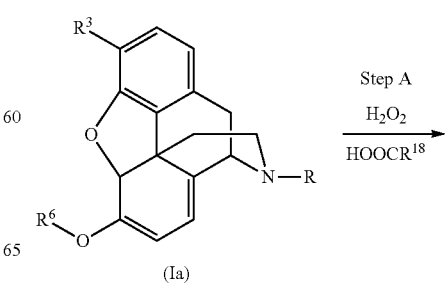

(Ia)

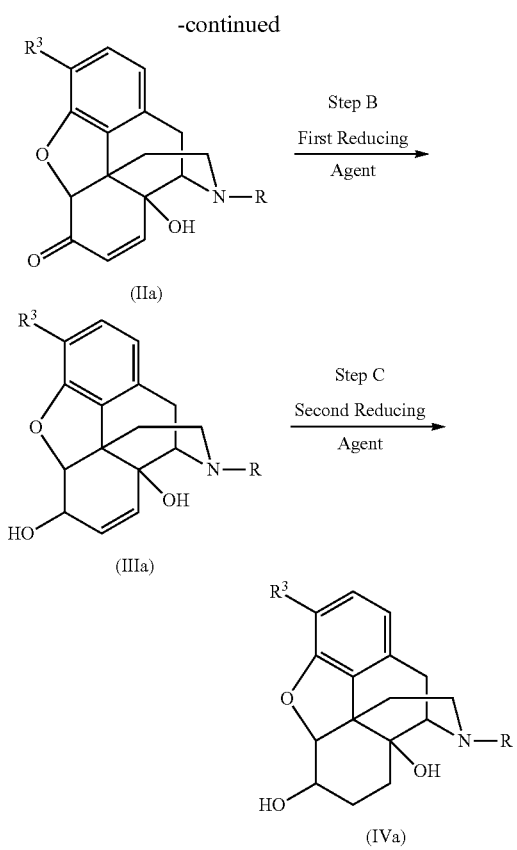

wherein:

R is selected from the group consisting of hydrogen, methyl, cyclopropyl methyl, cyclobutyl methyl, and allyl;

$R^3$ is selected from the group consisting of hydroxyl, alkoxy, aryloxy, substituted aryloxy, and protected hydroxy;

$R^6$ is selected from the group consisting of alkyl, aryl, substituted alkyl, and substituted aryl; and $R^{18}$ is selected from the group consisting of hydrogen, methyl, phenyl, and substituted phenyl.

In particular embodiments, $R^{18}$ may be hydrogen. In specific embodiments, R may be methyl, $R^3$ may be hydroxy, methoxy, or protected hydroxy, and $R^6$ may be methyl.

In some embodiments, the mole to mole ratio of the compound comprising Formula (Ia) to hydrogen peroxide to the compound comprising the formula $HOOCR^{18}$ may be from about 1:0.6:1 to about 1:2.2:8. In other embodiments, the process may be conducted in the presence of at least one polar, aprotic solvent; and the volume to mass ratio of the solvent to the compound comprising Formula (Ia) is from about 1:1 to about 4:1. In still other embodiments, the process may be conducted at a temperature from about 0° C. to about 70° C.

In exemplary embodiments, the first reducing agent comprises a borohydride. In a particular embodiment, the first reducing agent may be sodium borohydride or sodium triacetoxyborohydride. In another embodiment, the mole to mole ratio of the compound comprising Formula (IIa) to hydride from the first reducing agent may be from about 1:0.7 to about 1:5.

In one embodiment, the second reducing agent may be a hydrogen transfer reagent and the reduction is conducted in the presence of a transition metal catalyst. In an exemplary embodiment, the transition metal may be palladium supported on carbon. In other embodiments, the mole to mole ratio of the compound comprising Formula (IIIa) to the hydrogen transfer reagent to the transition metal catalyst may be from about 1:0.1:0.002 to about 1:1:0.02.

In one exemplary embodiment, the organic acid is formic acid (i.e., $R^{18}$ is hydrogen) and the second reducing agent is a hydrogen transfer reagent, wherein the hydrogen transfer reagent is formic acid. The hydrogen transfer reaction is conducted in the presence of a transition metal catalyst, such as palladium on carbon.

In some embodiments, steps (a), (b), and (c) may be conducted in a single reaction pot without isolation of the compounds comprising Formula (IIa) or Formula (IIIa). In other embodiments, the process may further comprise, after step (c), adjusting the pH to greater than about 8.7 to precipitate the compound comprising Formula (IVa). In yet other embodiments, the process may further comprise removing the hydroxyl group from C-14 of the compound comprising Formula (IVa). In exemplary embodiments, the compounds comprising Formulas (Ia), (IIa), (IIIa), or (IVa) independently have an optical activity of (−) or (+); and the configuration of C-5, C-13, C-14, and C-9, respectively, is RRRR, RRSR, RRRS, RRSS, RSRR, RSSR, RSRS, RSSS, SRRR, SRSR, SRRS, SRSS, SSRR, SSSR, SSRS, or SSSS, provided that the C-15 and the C-16 carbons are both either on the alpha face of the molecule or the beta face of the molecule. In still other embodiments, the hydroxy group on C-6 of the compounds comprising Formulas (IIIa) or (IVa) may have an alpha isomer to beta isomer ratio of at least 95:5.

(i) Downstream Applications

In some embodiments, the compound comprising Formula (I), (Ia), (II), (IIa), (III), (IIIa), (IV), or (IVa) may be converted into a pharmaceutically acceptable salt. The term "pharmaceutically-acceptable salts" are salts commonly used to form alkali metal salts and to form addition salts of free acids or free bases. The nature of the salt may vary, provided that it is pharmaceutically acceptable. Suitable pharmaceutically acceptable acid addition salts of compounds comprising Formula (IV) or (IVa) may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, examples of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, algenic, hydroxybutyric, salicylic, galactaric and galacturonic acid. Suitable pharmaceutically-acceptable base addition salts include metallic salts made from aluminum, calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding compound by reacting, for example, the appropriate acid or base with the any compound comprising Formula (I), (Ia), (II), (IIa), (III), (IIIa), (IV), or (IVa).

In other embodiments, the compound comprising Formula (I), (Ia), (II), (IIa), (III), (IIIa), (IV), or (IVa) may be converted into a "nal" compound, such as, e.g., naloxone, naltrexone, nalbuphene, nalmefene, or nalfurafine, by contact with a suitable N-alkylating agent. In still other embodiments, the compound comprising Formula (IV) or (IVa) may be derivatized to form a compound such as buprenorphine, etorphine, dihydroetorphine, diprenorphine, and the like.

(j) Stereochemistry

The compound comprising any of Formula (I), (Ia), (II), (IIa), (III), (IIIa), (IV), or (IVa) may have a (−) or a (+) orientation with respect to the rotation of polarized light. More specifically, each chiral center of the morphinans or normorphinans may have an R or an S configuration. The compounds described herein may have at least four chiral centers, namely carbons C-5, C-9, C-13, and C-14. At each chiral center, the stereochemistry at the carbon atom is independently R or S. The configuration of C-5, C-9, C-13, and C-14, respectively, may be RRRR, RRRS, RRSR, RSRR, SRRR, RRSS, RSSR, SSRR, SRRS, SRSR, RSRS, RSSS, SRSS, SSRS, SSSR, or SSSS, provided that the C-15 and C-16 atoms are both on the alpha face of the molecule or both on the beta face of the molecule.

The hydroxy group on C-6 of the compounds comprising Formula (III), (IIIa), (IV), or (IVa) exist as alpha isomers or beta isomers. The alpha isomer to beta isomer ratio of any of these compounds may be from about 50:50 to about 100:0. In exemplary embodiments, the alpha isomer to beta isomer ratio may be at least about 80:20, about 90:10, about 95:5, about 96:4, about 97:3, about 98:2, about 99:1, about 99.5:0.5, about 99.9:0.01, or about 99.95:0.05.

Definitions

The compounds described herein have asymmetric centers. Compounds of the present invention containing an asymmetrically substituted atom may be isolated in optically active or racemic form. All chiral, diastereomeric, racemic forms and all geometric isomeric forms of a structure are intended, unless the specific stereochemistry or isomeric form is specifically indicated.

The term "acyl," as used herein alone or as part of another group, denotes the moiety formed by removal of the hydroxy group from the group COOH of an organic carboxylic acid, e.g., RC(O)—, wherein R is $R^1$, $R^1O$—, $R^1R^2N$—, or $R^1S$—, $R^1$ is hydrocarbyl, heterosubstituted hydrocarbyl, or heterocyclo, and $R^2$ is hydrogen, hydrocarbyl, or substituted hydrocarbyl.

The term "acyloxy," as used herein alone or as part of another group, denotes an acyl group as described above bonded through an oxygen linkage (O), e.g., RC(O)O— wherein R is as defined in connection with the term "acyl."

The term "alkyl" as used herein describes groups which are preferably lower alkyl containing from one to eight carbon atoms in the principal chain and up to 20 carbon atoms. They may be straight or branched chain or cyclic (i.e., cycloalkyl) and include methyl, ethyl, propyl, isopropyl, butyl, hexyl and the like.

The term "alkenyl" as used herein describes groups which are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

The term "alkynyl" as used herein describes groups which are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "aromatic" as used herein alone or as part of another group denotes optionally substituted homo- or heterocyclic conjugated planar ring or ring system comprising delocalized electrons. These aromatic groups are preferably monocyclic (e.g., furan or benzene), bicyclic, or tricyclic groups containing from 5 to 14 atoms in the ring portion. The term "aromatic" encompasses "aryl" groups defined below.

The terms "aryl" or "Ar" as used herein alone or as part of another group denote optionally substituted homocyclic aromatic groups, preferably monocyclic or bicyclic groups containing from 6 to 10 carbons in the ring portion, such as phenyl, biphenyl, naphthyl, substituted phenyl, substituted biphenyl, or substituted naphthyl.

The terms "carbocyclo" or "carbocyclic" as used herein alone or as part of another group denote optionally substituted, aromatic or non-aromatic, homocyclic ring or ring system in which all of the atoms in the ring are carbon, with preferably 5 or 6 carbon atoms in each ring. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

The terms "halogen" or "halo" as used herein alone or as part of another group refer to chlorine, bromine, fluorine, and iodine.

The term "heteroatom" refers to atoms other than carbon and hydrogen.

The term "heteroaromatic" as used herein alone or as part of another group denotes optionally substituted aromatic groups having at least one heteroatom in at least one ring, and preferably 5 or 6 atoms in each ring. The heteroaromatic group preferably has 1 or 2 oxygen atoms and/or 1 to 4 nitrogen atoms in the ring, and is bonded to the remainder of the molecule through a carbon. Exemplary groups include furyl, benzofuryl, oxazolyl, isoxazolyl, oxadiazolyl, benzoxazolyl, benzoxadiazolyl, pyrrolyl, pyrazolyl, imidazolyl, triazolyl, tetrazolyl, pyridyl, pyrimidyl, pyrazinyl, pyridazinyl, indolyl, isoindolyl, indolizinyl, benzimidazolyl, indazolyl, benzotriazolyl, tetrazolopyridazinyl, carbazolyl, purinyl, quinolinyl, isoquinolinyl, imidazopyridyl, and the like. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics as described above. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The term "oxygen-protecting group" as used herein denotes a group capable of protecting an oxygen atom (and hence, forming a protected hydroxyl group), wherein the protecting group may be removed, subsequent to the reaction for which protection is employed, without disturbing the remainder of the molecule. The protected hydroxyl group may be designated by the terms "hydrocarbyloxy or substituted hydrocarbyloxy. Exemplary oxygen protecting groups include ethers (e.g., allyl, triphenylmethyl (trityl or Tr), p-methoxybenzyl (PMB), p-methoxyphenyl (PMP)), acetals (e.g., methoxymethyl (MOM), β-methoxyethoxymethyl (MEM), tetrahydropyranyl (THP), ethoxy ethyl (EE), methylthiomethyl (MTM), 2-methoxy-2-propyl (MOP), 2-trimethylsilylethoxymethyl (SEM)), esters (e.g., benzoate (Bz), allyl carbonate, 2,2,2-trichloroethyl carbonate (Troc), 2-trimethylsilylethyl carbonate), silyl ethers (e.g., trimethylsilyl (TMS), triethylsilyl (TES), triisopropylsilyl (TIPS), triphenylsilyl (TPS), t-butyldimethylsilyl (TBDMS), t-butyldiphenylsilyl (TBDPS) and the like. A variety of oxygen protecting groups and the synthesis thereof may be found in "Greene's Protective Groups in Organic Synthesis," 4$^{th}$ Ed. by P. G. M. Wuts and T. W. Greene, John Wiley & Sons, Inc., 2007.

The "substituted hydrocarbyl" moieties described herein are hydrocarbyl moieties which are substituted with at least one atom other than carbon, including moieties in which a carbon chain atom is substituted with a heteroatom such as nitrogen, oxygen, silicon, phosphorous, boron, or a halogen atom, and moieties in which the carbon chain comprises additional substituents. These substituents include alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

Having described the invention in detail, it will be apparent that modifications and variations are possible without departing from the scope of the invention defined in the appended claims.

EXAMPLES

The following examples are included to demonstrate certain embodiments of the invention. It should be appreciated by those of skill in the art that the techniques disclosed in the examples represent techniques discovered by the inventors to function well in the practice of the invention. Those of skill in the art should, however, in light of the present disclosure, appreciate that many changes can be made in the specific embodiments that are disclosed and still obtain a like or similar result without departing from the spirit and scope of the invention, therefore all matter set forth is to be interpreted as illustrative and not in a limiting sense.

Example 1

Oxidation of Thebaine to 14-Hydroxycodeinone

Thebaine (20.0 g, 64.2 mmol) was dissolved in 25% formic acid (50.0 g, 257 mmol, 4.0 eq.). Hydrogen peroxide (4.8 g, 50% in water, 70.0 mmol, 1.1 eq.) was added dropwise to the reaction mixture over a 1-hour period while maintaining the reaction temperature at 20-35° C. The solution was stirred at room temperature (20-25° C.) overnight and then heated at 50° C. for 6 hours, resulting in complete consumption of thebaine (COR<0.05%). The desired oxidation products, 14-hydroxycodeinone and 14-hydroxycodeinone N-oxide, were formed in 85% area (54.5 mmol) and 5% area (3.2 mmol), respectively, as measured by HPLC.

Example 2

Reduction of 14-Hydroxycodeinone to Oxycodol Via 14-Hydroxycodeine

To a flask, one-third of the final solution from Example 1 (about 21 mmol), isopropyl alcohol (7.5 g, 9.5 mL) and acetic acid (1.0 g, 0.95 mL) were added. The solution was stirred over a cooling bath (0-20° C.) after the pH was adjusted to 6.5 with concentrated ammonium hydroxide. Sodium borohydride (0.5 g, 13.21 mmol, 2.5 eq.) was added in four equal portions over the course of an hour, during which time the temperature of the reaction mixture was kept below 30° C. After addition, 14-hydroxycodeinone and 14-hydroxycodeinenone N-oxide, were completely converted into 14-hydroxycodeine (83% area) and 14-hydroxycodeine N-oxide (5.5% area), respectively, as measured by HPLC.

The reaction mixture was heated at 50° C. for 2 hours, after which 5% palladium on carbon (0.33 g, 0.15 mmol of Pd, 0.007 eq.) was added, acidified with formic acid (1.0 g, 0.82 mL), and continued to heat at 50° C. for additional 2 hours. The charcoal was filtered off, and the filtrate was cooled down to room temperature to give a clear solution of oxycodol (89% area by HPLC).

The pH was adjusted to 10.5 with 50% aqueous NaOH to give precipitant that was stirred for 1 hour at room temperature and filtered. The wet cake collected on a filter was washed with water (6.6 mL) and dried in an oven at 65° C. for 18 hours to give oxycodol as white solids (5.19 g) with purity of oxycodol in 99.55% area and a 6α-oxycodol to 6β-oxycodol ratio of 98.17:1.38 (71.1:1).

Example 3

Reduction of 14-Hydroxycodeinone to Oxycodol Via 14-Hydroxycodeine

To a flask, one-third of the final solution from Example 1 (about 21 mmol), isopropyl alcohol (5.0 g, 6.3 mL) and acetic acid (1.3 g, 1.2 mL) were added. The solution was stirred over a cooling bath (0-20° C.) after the pH was adjusted to 6.5 with concentrated ammonium hydroxide. Sodium triacetoxyborohydride (6.7 g, 31.6 mmol, 1.5 eq.) was added in four equal portions over a course of an hour, during which time the temperature of the reaction mixture was kept below 30° C. After addition, 14-hydroxycodeinone and 14-hydroxycodeinenone N-oxide, were completely converted into 14-hydroxycodeine (79.3% area) and 14-hydroxycodeine N-oxide (5.4% area), respectively, as measured by HPLC.

The reaction mixture was heated at 50° C. for 4 hours, after which 5% palladium on carbon (0.33 g, 0.15 mmol of Pd, 0.007 eq.) was added, acidified with formic acid (2.0 g, 1.6 mL), continued to heat at 50° C. for additional 4 hours. The charcoal was filtered off, and the filtrate was cooled to room temperature, giving a clear solution of oxycodol (87.8% area by HPLC).

The pH was adjusted to 10.5 with 50% aqueous NaOH to give precipitant that was stirred for 1 hour at room temperature and filtered. The wet cake collected on a filter was washed with water (6.6 mL) and dried in oven at 65° C. for 18 hours to give oxycodol as a white solid (5.12 g) with a purity of oxycodol in 99.06% area and a 6α-oxycodol to 6β-oxycodol ratio of 99.03:0.03 (3300:1).

Example 4

Oxidation of Thebaine to 14-Hydroxycodeinone

Thebaine (40.0 g, 128.4 mmol) was dissolved in 25% formic acid (50.0 g, 257 mmol, 2.0 eq.). Hydrogen peroxide (9.6 g, 50% in water, 140 mmol, 1.1 eq.) was added dropwise to the reaction mixture over a 1-hour period while maintaining the reaction temperature at 20-35° C. The solution was heated at 50° C. for 10 hours, which resulted in a complete consumption of thebaine (COR<0.05%). The desired oxidation products, 14-hydroxycodeinenone and 14-hydroxycodeinenone N-oxide, were formed in 85% area and 4% area respectively.

Example 5

Reduction of 14-Hydroxycodeinone to Oxycodol Via 14-Hydroxycodeine

To a flask, one-sixth of the final solution from Example 4 (about 21 mmol), isopropyl alcohol (10 g, 12.5 mL) and acetic acid (2.0 g, 1.9 mL) were added. The solution was stirred over a cooling bath (0-20° C.) after the pH was adjusted to 6.5 with concentrated ammonium hydroxide. Sodium borohydride (0.5 g, 13.2 mmol, 2.4 eq.) was added in four equal portions over a course of an hour, during which time the temperature of the reaction mixture was controlled below 30° C. After addition, 14-hydroxycodeinone and 14-hydroxycodeinenone N-oxide, were completely converted into 14-hydroxycodeine (83.4% area) and 14-hydroxycodeine N-oxide (4.24% area), respectively, as measured by HPLC.

The reaction mixture was heated at 50° C. for 4 hours, after which 5% palladium on carbon (0.33 g, 0.15 mmol of Pd, 0.007 eq.) was added, acidified with formic acid (2.0 g, 1.6 mL), and continued to heat at 50° C. for additional 4 hours. The charcoal was filtered off, and the filtrate cooled down to room temperature, giving a clear solution of oxycodol (91.2% area by HPLC).

The pH was adjusted to 10.5 using 50% aqueous NaOH to give precipitants that were stirred for 1 hour at room temperature and filtered. The wet cake collected on a filter was washed with water (6.6 mL) and dried in oven at 65° C. for 18 hours to give oxycodol as white solids (5.33 g) with purity of 99.12% and a 6α-oxycodol to 6β-oxycodol ratio of 98.41:0.71 (138:1).

Example 6

Reduction of 14-Hydroxycodeinone to Oxycodol Via 14-Hydroxycodeine

To a flask, half of the final solution from Example 4 (about 64 mmol), isopropyl alcohol (7.5 g, 9.5 mL) and acetic acid (4.0 g, 3.8 mL) were added. The solution was stirred over a cooling bath (0-20° C.) after the pH was adjusted to 6.5 with concentrated ammonium hydroxide. Sodium borohydride (0.96 g, 25.37 mmol, 1.6 eq.) was added in four equal portions over a course of an hour, during which time the temperature of the reaction mixture was kept below 30° C. After addition, 14-hydroxycodeinone and 14-hydroxycodeinenone N-oxide, were completely converted into 14-hydroxycodeine (78.16% area) and 14-hydroxycodeine N-oxide (4.26% area), respectively, as measured by HPLC.

The reaction mixture was heated at 60° C. for 3 hours, after which 5% palladium on carbon (0.60 g, 0.28 mmol, 0.004 eq.) was added, acidified with formic acid (3.0 g), and continued to heat at 60° C. for additional 8 hours. The charcoal was filtered off charcoal, and the filtrate was cooled to room temperature, giving a clear solution of oxycodol (84.88% area by HPLC).

Example 7

Isolation of Oxycodol Hydrochloride Directly from the Reaction Mixture

Half of the final solution from Example 6 (about 64 mmol) was transferred into a flask. After pH was adjusted to 10 with 50% aqueous sodium hydroxide, the mixture was stirred at room temperature for 10 minutes and extracted with chloroform (60 g, 40.5 mL). The organic layer was separated, washed with water (60 g, 60 mL) and filtered. The filtrate was diluted with isopropyl alcohol (60 g, 76 mL) and a portion of the solvent (60 mL) was removed by distillation. Ethyl acetate (60 g, 67 mL) and then 37% HCl was added to adjust pH to be less than 3.5. The suspension formed was stirred at 60° C. for 1 hour, cooled down to room temperature for 1 hour, and filtered. The wet cake collected on a filter was washed with isopropyl alcohol (20 mL) and dried in oven at 65° C. for 18 hours to give 8.35 g of oxycodol hydrochloride as white solids with purity of 96.01% and a 6α-oxycodol to 6β-oxycodol ratio of 95.00:1.01 (95:1).

Example 8

Isolation of Oxycodol Hydrochloride Directly from the Reaction Mixture

The second half of the final solution of Example 6 (about 64 mmol) was transferred into a flask. After pH was adjusted to 10 with 50% aqueous sodium hydroxide, the mixture was stirred at room temperature for 10 minutes and extracted with ethyl acetate (60 g, 67 mL). The aqueous layer was separated and extracted with ethyl acetate (20 g, 22 mL). The combined organic layers were washed with water (20 g, 20 mL) and filtered. To the filtrate, 37% HCl was added until pH<3.5. The suspension formed was stirred at 60° C. for 1 hour, cooled down to room temperature, and filtered. The wet cake collected on a filter was washed with ethyl acetate (20 mL) and dried in oven at 65° C. for 18 hours, giving 8.18 g of oxycodol hydrochloride as a white solid with purity of 99.45% and a 6α-oxycodol to 6β-oxycodol ratio of 98.05:1.40 (70:1).

What is claimed is:

1. A process for preparing a compound of Formula (IV) from a compound of Formula (I), comprising:
   (a) contacting the compound of Formula (I) with hydrogen peroxide and a compound of formula HOOCR$^{18}$ to form a compound of Formula (II);
   (b) contacting the compound of Formula (II) with a first reducing agent to form a compound of Formula (III); and
   (c) contacting the compound of Formula (III) with a second reducing agent to form the compound of Formula (IV) according to the following reaction scheme:

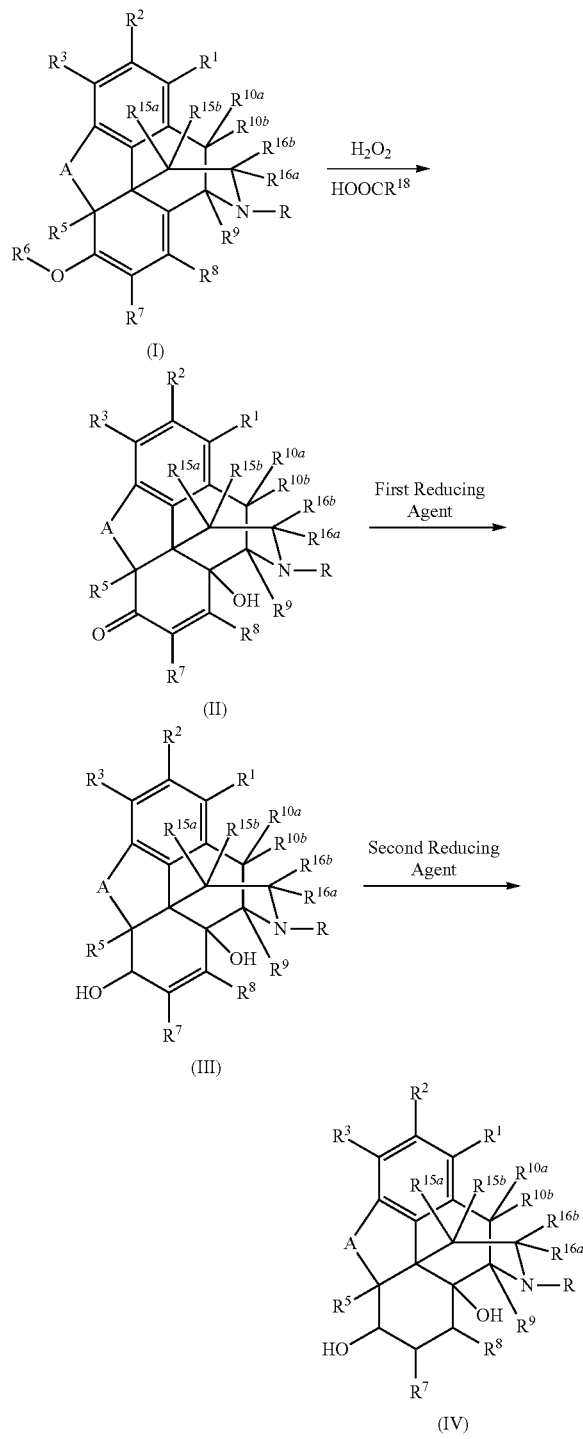

wherein:
A is oxygen;
R is selected from the group consisting of hydrogen, hydrocarbyl, and substituted hydrocarbyl;
$R^1$, $R^2$, and $R^3$ are independently selected from the group consisting of hydrogen, amino, halogen, {—}OH, {—}$OR^{1611}$, {—}SH, {—}$SR^{1611}$, {—}$NHR^{1611}$, {—}$NR^{1611}R^{1612}$, hydrocarbyl, and substituted hydrocarbyl;
$R^5$, $R^7$, $R^8$, $R^9$, $R^{10a}$, $R^{10b}$, $R^{15a}$, $R^{15b}$, $R^{16a}$, and $R^{16b}$ are independently selected from the group consisting of hydrogen, amino, halogen, {—}OH, {—}$OR^{1611}$, {—}SH, {—}$SR^{1611}$, {—}$NHR^{1611}$, {—}$NR^{1611}R^{1612}$, hydrocarbyl, and substituted hydrocarbyl; wherein any pair of $R^{\#a}$ and $R^{\#b}$ wherein # is any one of 10, 15, and 16, optionally together form a moiety chosen from the group consisting of {=}O, {=}S, {=}$CH_2$, and {=}$NR^{1612}$;
$R^6$, $R^{1611}$, and $R^{1612}$ are independently selected from the group consisting of hydrocarbyl and substituted hydrocarbyl; and
$R^{18}$ is selected from the group consisting of hydrogen, hydrocarbyl and substituted hydrocarbyl.

2. The process of claim 1, wherein
R is selected from the group consisting of hydrogen, alkyl, alkenyl, alkynyl, aryl, substituted alkyl, substituted alkenyl, substituted alkynyl, and substituted aryl;
$R^1$ and $R^2$ are independently selected from the group consisting of hydrogen, amino, amine, halo, hydroxy, alkoxy, alkyl, alkenyl, alkynyl, aryl, substituted alkyl, substituted alkenyl, substituted alkynyl, and substituted aryl;
$R^3$ is selected from the group consisting of hydroxy, alkoxy, hydrocarbyloxy, and substituted hydrocarbyloxy;
$R^6$ is selected from the group consisting of alkyl, alkenyl, alkynyl, aryl, substituted alkyl, substituted alkenyl, substituted alkynyl, and substituted aryl;
$R^5$, $R^7$, $R^8$, $R^9$, $R^{10a}$, $R^{15a}$, $R^{15b}$, $R^{16a}$, and $R^{16b}$ are independently selected from the group consisting of hydrogen, amino, amine, halo, hydroxy, alkoxy, alkyl, alkenyl, alkynyl, aryl, substituted alkyl, substituted alkenyl, substituted alkynyl, and substituted aryl; and
$R^{18}$ is selected from the group consisting of hydrogen, alkyl, aryl, substituted alkyl, and substituted aryl.

3. The process of claim 2, wherein; R is selected from the group consisting of hydrogen, methyl, cyclopropyl methyl, cyclobutyl methyl, and allyl; $R^1$, $R^2$, $R^5$, $R^7$, $R^8$, $R^9$, $R^{10a}$, $R^{10b}$, $R^{15a}$, $R^{15b}$, $R^{16a}$, and $R^{16b}$ if present, are hydrogen; $R^3$ is selected from the group consisting of hydroxy, alkoxy, aryloxy, substituted aryloxy, and protected hydroxy; $R^6$ is selected from the group consisting of alkyl and aryl; and $R^{18}$ is selected from the group consisting of hydrogen, methyl, phenyl, and substituted phenyl.

4. The process of claim 1, wherein the mole to mole ratio of the compound of Formula (I) to hydrogen peroxide to the compound comprising formula $HOOCR^{18}$ is from about 1:0.1:0.2 to about 1:11:40.

5. The process of claim 1, wherein the first reducing agent comprises a borohydride.

6. The process of claim 5, wherein the mole to mole ratio of the compound of Formula (II) to hydride from the first reducing agent is from about 1:0.15 to about 1:25.

7. The process of claim 1, wherein the second reducing agent is selected from the group consisting of a hydrogen transfer reagent, a combination of a hydrogen transfer reagent and a metal catalyst, and hydrogen and a metal catalyst.

8. The process of claim 1, wherein the second reducing agent is a hydrogen transfer reagent, and the hydrogen transfer reagent is used in the presence of a transition metal catalyst.

9. The process of claim 8, wherein the mole to mole ratio of the compound of Formula (III) to the hydrogen transfer reagent to the transition metal catalyst is from about 1:0.5: 0.0004 to about 1:10:0.08.

10. The process of claim 1, wherein the process is conducted in the presence of at least one polar protic solvent; and the volume to mass ratio of the solvent to the compound of Formula (I) is from about 0.5:1 to about 100:1.

11. The process of claim 1, wherein the process is conducted at a temperature from about 0° C. to about 100° C.

12. The process of claim 1, wherein steps (a), (b), and (c) are conducted in a single reaction pot without isolation of the compounds of Formula (II) or Formula (III).

13. The process of claim 1, further comprising, after step (c), adjusting the pH to greater than about 8.7 to precipitate the compound of Formula (IV).

14. The process of claim 1, further comprising removing the hydroxyl group from C-14 of the compound of Formula (IV).

15. The process of claim 1, wherein the compounds of Formulas (I), (II), (III), and (IV) independently have an optical activity of (−) or (+); and the configuration of C-5, C-13, C-14, and C-9, respectively, is RRRR, RRSR, RRRS, RRSS, RSRR, RSSR, RSRS, RSSS, SRRR, SRSR, SRRS, SRSS, SSRR, SSSR, SSRS, or SSSS, provided that the C-15 and the C-16 carbons are both either on the alpha face of the molecule or the beta face of the molecule.

16. The process of claim 1, wherein the hydroxy group on C-6 of the compounds of Formulas (III) or (IV) has an alpha isomer to beta isomer ratio of at least 90:10.

17. The process of claim 3, wherein $R^{18}$ is hydrogen; the first reducing agent is sodium borohydride or sodium triacetoxyborohydride; the second reducing agent is a hydrogen transfer agent which is used in the presence of a transition metal catalyst, and the hydrogen transfer agent is formic acid.

18. The process of claim 17, wherein the mole to mole ratio of the compound of Formula (I) to hydrogen peroxide to the compound of formula $HOOCR^{18}$ is from about 1:0.6:1 to about 1:2.2:8; the mole to mole ratio of the compound of Formula (II) to hydride from the first reducing agent is from about 1:0.7 to about 1:5; the mole to mole ratio of the compound of Formula (III) to the hydrogen transfer reagent to the transition metal catalyst is from about 1:0.1:0.002 to about 1:1:0.02.

19. The process of claim 18, wherein the process is conducted in the presence of at least one polar protic solvent; and the volume to mass ratio of the solvent to the compound of Formula (I) is from about 1:1 to about 20:1, and the process is conducted at a temperature from about 0° C. to about 70° C.

20. The process of claim 19, further comprising removing the hydroxyl group from C-14 of the compound of Formula (IV).

* * * * *